US005470424A

United States Patent [19]
Isaac et al.

[11] Patent Number: 5,470,424
[45] Date of Patent: Nov. 28, 1995

[54] PROCESS FOR FORMING LIQUID IMPERMEABLE SHEET MATERIAL HAVING A FIBROUS SURFACE AND PRODUCTS FORMED THEREBY

[75] Inventors: Robert L. Isaac, Bethesda, Md.; Bernard Cohen, Berkeley Lake; Lee K. Jameson, Roswell, both of Ga.

[73] Assignee: Kimberly-Clark Corporation, Neenah, Wis.

[21] Appl. No.: 159,979

[22] Filed: Nov. 30, 1993

[51] Int. Cl.⁶ ............... B32B 31/20; B32B 17/02; D04H 1/58
[52] U.S. Cl. .............. 156/253; 428/284; 428/283; 428/288; 428/296; 428/286; 428/298; 156/309.6
[58] Field of Search ............... 428/273, 284, 428/286, 287, 297, 298, 299, 326, 288, 296; 604/378, 366, 370, 372, 383; 427/245; 156/296, 308.2, 309.6, 253, 268

[56] References Cited

U.S. PATENT DOCUMENTS

| | | | |
|---|---|---|---|
| 2,689,199 | 9/1954 | Pesce | 154/46 |
| 3,532,589 | 10/1970 | David | 428/296 |
| 3,734,800 | 5/1973 | Ryan | 156/309 |
| 4,315,965 | 2/1982 | Mason et al. | 428/198 |
| 4,342,813 | 8/1982 | Erickson | 428/296 |
| 4,582,750 | 4/1986 | Lou et al. | 428/288 |
| 4,613,544 | 9/1986 | Burleigh | 428/315.5 |
| 4,684,568 | 8/1987 | Lou | 428/265 |
| 4,747,846 | 5/1988 | Boland et al. | 604/38 A |
| 4,886,512 | 12/1989 | Damico et al. | 609/385.2 |
| 4,898,761 | 2/1990 | Dunaway et al. | 428/137 |
| 4,939,036 | 7/1990 | Reith | 428/349 |
| 4,973,326 | 11/1990 | Wood et al. | 604/391 |
| 4,994,054 | 2/1991 | Pigneul et al. | 604/391 |
| 5,019,073 | 5/1991 | Roessler et al. | 604/391 |
| 5,032,450 | 7/1991 | Rechlicz | 428/196 |
| 5,176,670 | 1/1993 | Roessler et al. | 604/391 |
| 5,176,672 | 1/1993 | Bruemmer et al. | 604/385.1 |
| 5,192,606 | 3/1993 | Proxmire et al. | 428/284 |
| 5,208,098 | 5/1993 | Stover | 428/284 |
| 5,219,341 | 6/1993 | Serbiak et al. | 604/361 |
| 5,221,275 | 6/1993 | Van Iten | 604/387 |
| 5,269,981 | 12/1993 | Jameson et al. | 264/23 |

FOREIGN PATENT DOCUMENTS 258015  3/1988  European Pat. Off. .

OTHER PUBLICATIONS

U.S. Application S/N 08/171,937 "Non-Invasive Adhesive Process" filed Dec. 22, 1993, (Isaac et al.).

Primary Examiner—George F. Lesmes
Assistant Examiner—Kathryne E. Shelborne
Attorney, Agent, or Firm—Joseph P. Harps

[57] ABSTRACT

Disclosed are a number of processes for forming a liquid-impermeable sheet having a fibrous cloth-like surface. In one embodiment the process includes the steps of: (1) forming a sheet having first and second fibrous surfaces; and subjecting the sheet to pressure and a z-gradient temperature differential sufficient to melt the fibers of the first surface and form the melt into a liquid impermeable skin without significantly altering the fibers of the second surface. In another embodiment, the process includes the steps of: (1) forming a sheet having first and second fibrous surfaces wherein, upon the sheet being subjected to a sufficient temperature, the fibers forming the first fibrous surface are adapted to substantially completely melt prior to the fibers forming the second fibrous surface significantly melting; and (2) subjecting the sheet to a sufficient pressure and temperature to melt the fibers of the first surface and form the melt into a liquid impermeable skin without significantly altering the fibers of the second surface. In some embodiments the liquid impermeable skin is subsequently apertured to make the sheet breathable. Products formed by these processes are also disclosed.

33 Claims, 2 Drawing Sheets

PROCESS FOR FORMING LIQUID IMPERMEABLE SHEET MATERIAL HAVING A FIBROUS SURFACE AND PRODUCTS FORMED THEREBY

BACKGROUND OF THE INVENTION

Sheet materials having one or more fibrous surfaces are well known to those in the art. Examples of such materials are nonwoven web materials. In recent years nonwoven web materials such as, for example, meltblown and spunbonded materials, have gained significant market recognition and acceptance as compared to more conventional woven textile materials when the material is to be used in a "disposable" application. As used herein, the term "disposable" is intended to include applications where a product is designed to be used once or a very limited number of times and then thrown away. Acceptance of the nonwoven web materials has been, at least in part, due to the highly favorable costs associated with the manufacture of the nonwoven web materials as compared to conventional weaving processes. For example, nonwoven web materials have significantly penetrated the manufacture of products such as disposable diapers, training pants, hospital gowns, surgical gowns, surgical drapes and environmentally protective clothing such as chemically protective and biologically protective clothing.

In spite of the penetration of the identified markets and others by nonwoven web materials, many products in these areas highly desire, if not require, the garment or other item to maintain a barrier against a given substance. This desirable attribute has virtually become a requirement in the medical area with the advent of the AIDS virus and the concomitant wish for doctors to remain isolated from patients' bodily fluids and vis versa. Typically, conventional nonwoven web material with its generally open porous structure cannot provide an absolute barrier against fluids such as gases and liquids or, for that fact, for small solid particulates such as dust or viruses.

Such an absolute barrier can typically only be obtained through the utilization of a film layer desired to act as a barrier to the substance or substances which are to remain isolated. Products formed from film layers have, indeed, been utilized. Unfortunately, such film-formed products suffer from a number of deficiencies. First, the product generally appears to be of a very cheap nature. Secondly, the product may well be quite uncomfortable as a result of the harsh hand or feel of a plastic film. Further, the product may well add to the discomfort of the wearer because plastic films typically cannot pass water vapor and the wearer's perspiration tends to build-up on the inside of the garment or on the wearer because it has no readily available avenue of escape.

In order to overcome the deficiencies of a garment manufactured from a film, those in the art have laminated films to nonwoven materials. Such a lamination, with the nonwoven web material being on an outer surface, gives the resultant composite a very pleasant hand. Furthermore, if the film is apertured, for example, microaperatured so that water vapor can pass through it, the comfort of the wearer is improved significantly. If the apertures in the film are small enough, the composite can be designed to be a generally effective barrier against quite a number of substances. While garments formed from nonwoven/film laminates have enjoyed success, a drawback associated with them is the increased cost of manufacture associated with the lamination process. In other words, to get the benefits of both a film material and a nonwoven material not only must both materials be used but the two must be married together in a costly lamination process. This places products made from such a laminate at a competitive disadvantage.

Accordingly, those of skill in the art have been searching for a process or processes where a liquid impermeable sheet can be formed which has a fibrous surface with a soft cloth-like hand and which avoids the costs associated with lamination and the utilization of disparate materials.

OBJECTS OF THE INVENTION

Accordingly, it is a general object of the present invention to provide a process for forming a liquid impermeable sheet material having a fibrous surface.

A further object of the present invention is to provide a process for forming a liquid impermeable sheet material having a fibrous surface which is breathable in that it can Is, ass water vapor.

It is yet another object of the present invention to provide the products which are formed by the aforementioned processes.

Still further objects and the broad scope of applicability of the present invention will become apparent to those of skill in the art from the details given hereinafter. However, it should be understood that the detailed description of the preferred embodiment of the present invention is given only by way of illustration because various changes and modifications well within the spirit and scope of the invention should become apparent to those of skill in that art in view of the following detailed description.

SUMMARY OF THE INVENTION

In response to the aforementioned difficulties encountered by those of skill in the art we have devised a number of processes for forming a liquid-impermeable sheet having a fibrous surface which greatly lessens, if not totally eliminates many of these problems. In one embodiment the process includes; the steps of: (1) forming a sheet having a first fibrous surface and a second fibrous surface, and (2) subjecting the sheet to pressure and a z-gradient temperature differential sufficient to generally completely melt the fibers of the first surface and form the melt into a liquid impermeable skin without significantly altering the fibers of the second surface.

While the temperature range of the z-gradient differential need only be sufficient to melt the fibers of the first surface without significantly altering the fibers of the second surface, it may be desirable for the z-gradient temperature differential to be at least about 140 degrees C. (284 degrees F.) For example, the z-gradient temperature differential may be at least about 150 degrees C. (302 degrees F.) More particularly, the z-gradient temperature differential may be at least about 160 degrees C. (320 degrees F.)

In another embodiment, the process includes the steps of: (1) forming a sheet having a first fibrous surface and a second fibrous surface wherein, upon the sheet being subjected to a sufficient temperature, the fibers forming the first fibrous surface are adapted to substantially completely melt prior to the fibers forming the second fibrous surface significantly melting; and (2) subjecting the sheet to a sufficient pressure and temperature to melt the fibers of the first surface and form the melt into a liquid impermeable skin without significantly altering the fibers of the second surface.

One of the ways that the preferential skin formation can be enhanced in either of these process variants is for the fibers forming the first surface to be formed from a material having a melt flow rate which is at least 25 percent greater than the melt flow rate of the material forming the fibers of the second surface. For example, the fibers forming the first surface may be formed from a material having a melt flow rate which is at least 50 percent greater than the melt flow rate of the material forming the fibers of the second surface. More particularly, the fibers forming the first surface may be formed from a material having a melt flow rate which is at least 100 percent greater than the melt flow rate of the material forming the fibers of the second surface.

Another way that the preferential skin formation can be enhanced in either process variant is for the fibers forming the first surface to have an average diameter which is at 1least about 50 percent less than the average diameter of the fibers forming the second surface. For example, the fibers forming the first surface may have an average diameter which is at least about 75 percent less than the average diameter of the fibers forming the second surface. More particularly, the fibers forming the first surface may have an average diameter which is at least about 90 percent less than the average diameter of the fibers forming the second surface.

The materials for forming the fibers which form the first and second surfaces of the sheet may generally be selected from any appropriate thermoplastic material. For example, exemplary materials for forming the fibers which form the first and second surfaces may be selected from one or more materials from the group of polyolefins, polyesters, polyamides, polyurethanes, polyetheresters and various copolymers of the monomers forming these materials with each other or other monomers. Blocks copolymers of various types may also be utilized.

The invention is also directed toward products which are formed by either of these processes.

The present invention is also directed toward a precursor sheet which is adapted to preferentially form a skin when subjected to sufficient temperature and pressure. The application of a z-gradient temperature differential to this sheet to effect skin formation is unnecessary. However, in some embodiments, a z-gradient temperature differential may be applied to such a sheet in order to hasten skin formation. The precursor sheet material conventionally includes: (1) a first fibrous surface; and (2) a second fibrous surface. The fibers forming the first and second surfaces differ in that, upon the sheet being subjected to a sufficient temperature, the fibers comprising the first fibrous surface are adapted to substantially completely melt prior to the fibers comprising the second fibrous surface significantly melting. Subsequent application of pressure forms the melt into the liquid impermeable skin layer.

As was stated above, one of the ways that the preferential skin formation can be enhanced in either of these process variants is for the fibers forming the first surface to be formed from a material having a melt flow rate which is at least 25 percent greater than the melt flow rate of the material forming the fibers of the second surface. For example, the fibers forming the first surface may be formed from a material having a melt flow rate which is at least 50 percent greater than the melt flow rate of the material forming the; fibers of the second surface. More particularly, the fibers forming the first surface may be formed from a material having a melt flow rate which is at least 100 percent greater than the melt flow rate of the material forming the fibers of the second surface.

Another way that the preferential skin formation can be enhanced in either process variant is for the fibers forming the first surface to have an average diameter which is at least about 50 percent less than the average diameter of the fibers forming the second surface. For example, the fibers forming the first surface may have an average diameter which is at least about 75 percent less than the average diameter of the fibers forming the second surface. More particularly, the fibers forming the first surface may have an average diameter which is at least about 90 percent less than the average diameter of the fibers forming the second surface.

In some embodiments either of the processes may also include the further step of aperturing the skin so that the resultant product is breathable. That is, the product remains liquid impervious while being able to pass water vapor. In some further embodiments the apertures may be microapertures.

In other embodiments either the processes may include the step of depositing fibers or particulates on the skin layer while the layer is still at least semi-molten so that the deposited fibers adhere to the skin layer. This process results is a material which either (1) has two fibrous surfaces with a film or skin layer sandwiched therebetween or (2) has a particulate bearing layer and a fibrous layer with a film or skin layer sandwiched therebetween.

THE FIGURES

TEST

Unless otherwise specified, melt flow is to be measured in accordance with ASTM D1238-90B (condition L). The units of melt flow rate are decigrams per minute or grams per ten minutes.

DEFINITIONS

As used herein, the term breathable requires that a material has a water vapor transmission rate of at least 500 grams per square meter per 24 hours. (ASTM E 96-80)

As used herein, the term liquid impermeable requires that a material have a hydrohead value of at least 50 centimeters of water. (Federal Test Method No. 5514, standard no. 191A.)

Average diameter of a fiber is determined by microscopy. The value is the average of five (5) random measurements.

DETAILED DISCLOSURE

Figure 1:
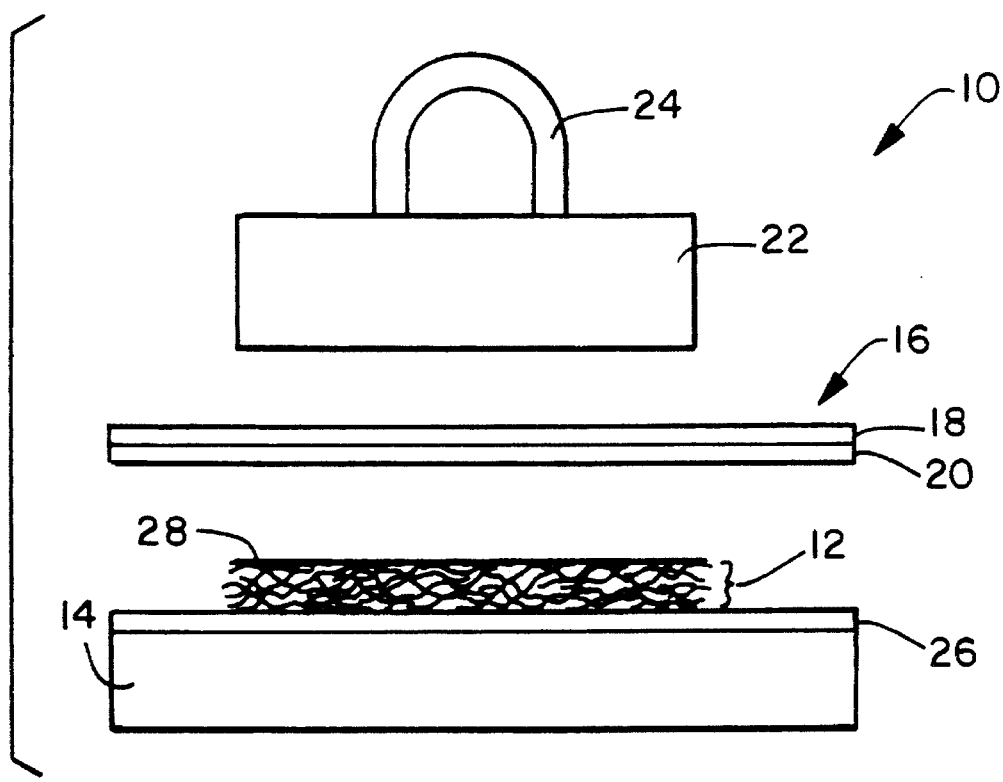
FIG. 1 is a schematic representation of an apparatus for performing present invention.

Turning now to the figures where like features are represented by like numerical reference numbers, and, in particular, it can be seen that FIG. 1 illustrates an apparatus 10 for forming a liquid impermeable sheet material having a fuzzy, cloth-like, fibrous surface. Initially, a fibrous web 12 such as, for example, a conventional meltblown web or a spunbonded web is placed on a heat sink 14. The heat sink 14 can be formed from, for example, a metal plate such as a steel, aluminum or copper plate. In some embodiments the heat sink 14 may be chilled by conventional means (not shown).

A composite sheet 16 is placed on top of the fibrous web 12 so that the fibrous web is completely covered thereby. The composite sheet 16 may be formed, for example, by a sheet of aluminum foil 18 which has a non-adhesive material 20 which has been coated onto one surface thereof. Alternatively, the composite sheet 16 may be a fiberglass cloth which has been impregnated with the non-adhesive material. If the composite sheet 16 is a coated aluminum foil 18, it is placed on the web 12 so that the non-adhesive surface coating 20 is adjacent the fibrous web 12. An exemplary non-adhesive coating 20 is sold under the trade designation "Teflon®" by the DuPont Company of Wilmington, Del.

A heating element 22 or plate such as, for example, a conventional iron or the heating element of a stirring hot plate having a steel plate attached to one surface thereof, can be used to apply heat and pressure to the web 12 by placing the heating plate 22 on the aluminum foil 18 side of the composite sheet 16 and conducting an ironing operation. That is, lightly pressing the iron down and moving it around over the composite sheet 16. The heating element 22, desirably, may be provided with thermally insulated handles 24 to assist in the ironing operation. The composite sheet 16 acts as a release agent between the fibrous web 12 and the heating element 22 and eliminates sticking of the fibrous web 12 to the heating element 22. In some embodiments it may be desirable to, additionally, provide the heat sink 14 with a resilient surface coating 26 to aid in the removal of the fibrous web 12 from the surface of the heat sink 14 after the application of thermal energy is complete. For example, the heat sink 14 can be provided with a silicon rubber coating of about 1/32nd inch in thickness. The resilient coating 26 on the surface of the heat sink 14 also acts to "level out" any imperfections which may be present in the surface of the heat sink 14 so that a generally uniform pressure is applied to the fibrous web 12.

Figure 2:
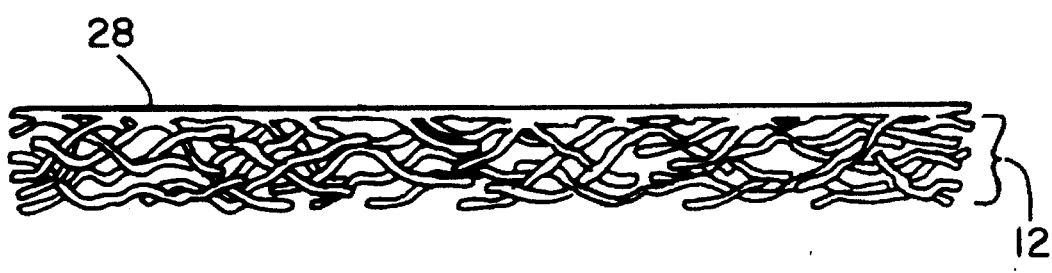
FIG. 2 is a cross-sectional view of a nonwoven web having a skin layer.

Proper selection of pressure, temperature and dwell time of the heating element 22 at a given point will result in the fibers on the surface of the fibrous web 12 adjacent the non-adhesive coating 20 to melt, flow and be formed into a thin liquid impermeable skin layer 28 without the fibrous nature of the fibers on the surface adjacent the heat sink 14 being significantly adversely affected. Of course, those of skill in the art will readily recognize that the pressure, temperature and dwell time variables will independently vary with respect to each other and also will vary depending upon the composition of the fibrous sheet 12. FIG. 2 illustrates a cross-section of a product 30 formed in accordance with the above teachings.

The skin layer 28 is formed because the fibrous web 12 is subjected both to pressure and a z-gradient temperature differential sufficient to generally completely melt the fibers of the first surface and the resultant melt into the liquid impermeable skin 28 without significantly altering the fibers of the second surface of the web 12. By z-gradient temperature differential, it is meant that the fibers of the first surface of the web 12 are subjected to a higher temperature than the fibers of the second surface of the fibrous web 12. For example, it may be desirable for the z-gradient temperature differential to be at least about 140 degrees C. (284 degrees F.) More particularly, the z-gradient temperature differential may be at least about 150 degrees C. (302 degrees F.) Even more particularly, the z-gradient temperature differential may be at least about 160 degrees C. (320 degrees F.)

Those of skill in the art will recognize that, if the fibrous web 12 is uniformly homogeneous in nature, the side of the fibrous web 12 placed on the heat sink 14 does not matter. However, fibrous webs 12 structured in this manner, i.e. 100 percent of the same polymer having a generally uniform average fiber diameter, significantly increase the difficulty of obtaining and maintaining an appropriate set of process variables (pressure, temperature, dwell time) which form a skin layer 28 while still not significantly adversely affecting the fibrous characteristic of the fibers of the second surface. Accordingly, an aspect of some embodiments of the present invention is that the fibrous web 12 is designed so that the fibers of the; first surface preferentially melt at either a lower temperature or at a faster rate at the same temperature as compared to the fibers of the second surface. Accordingly, if, such is the case, care should be taken to lay the fibrous web 12 on the heat sink 14 so that the surface of the fibrous web 12 which will be formed into the skin 28 will be nearest the heat element 22 during the application of thermal energy to the fibrous web 12.

While there are, no doubt, numerous mechanisms by which the fibrous web 12 can be designed or formed so that the fibers of the first surface preferentially melt before the fibers of the second surface or by which the fibers of the first surface melt at a faster rate than those forming the second surface, the following mechanisms for accomplishing this feature have been identified.

First, the fibrous web 12 can be formed by conventional means such as multi-bank meltblowing and/or multi-bank spunbonding processes, so that it is at least a two-layer structure with the polymer forming the fibers of the first surface having a lower melting point than the fibers forming the surface of the second surface. For example, the melting point differential may be at least 10 degrees Centigrade (C.). (50 degrees F.) More particularly, the melting point differential may be at least 100 degrees C. (212 degrees F.) Even more particularly, the melting point differential may be at least 200 degrees C. (392 degrees F.)

Figure 3:
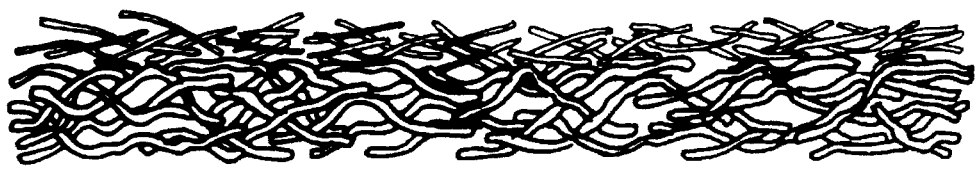
FIG. 3 is a cross-sectional view of a nonwoven web having a layer of thick fibers and a layer of thin fibers.

Another way that the preferential skin layer 28 formation can be enhanced is for the fibers forming the first surface to be formed from a material having a melt flow rate which is at least 25 percent greater than the melt flow rate of the material forming the fibers of the second surface. For example, the fibers forming the first surface may be formed from a material having a melt flow rate which is at least 50 percent greater than the melt flow rate of the material forming the fibers of the second surface. More particularly, the fibers forming the first surface may be formed from a material having a melt flow rate which is at least 100 percent greater than the melt flow rate of the material forming the fibers of the second surface. Yet another way that the preferential skin formation can be enhanced is for the fibers forming the first surface to have an average diameter which is at least about 50 percent less than the average diameter of the fibers forming the second surface. For example, the fibers forming the first surface may have an average diameter which is at least about 75 percent less than the average diameter of the fibers forming the second surface. More particularly, the fibers forming the first surface may have an average diameter which is at least about 90 percent less than the average diameter of the fibers forming the second surface. This feature is illustrated in FIG. 3 and is based upon the principle of the more efficient heat transfer characteristics of fibers having a smaller diameter as compared to those having larger diameters. In other words, generally speaking, assuming all other factors, including the polymer used, are the same, smaller diameter fibers will melt prior to larger diameter fibers melting. Thus, the fibrous web 12 could be formed from two layers of the same polymeric material with the fibers forming the first layer being small diameter, fine fibers and the fibers forming the second surface being larger diameter fibers. In such a situation, even if not subjected to a z-gradient temperature differential, the fibers of the first surface layer would generally completely melt prior to significant melting of the fibers of the second surface layer.

It is important to note that, in the event that the fibrous web 12 is designed to preferentially form a skin layer 28 on one side thereof, this feature, in many instances, eliminates the necessity of subjecting the fibrous web 12 to a z-gradient temperature differential. In other words, an application of thermal energy is still necessary but the thermal energy does not have to be applied in z-gradient fashion.

Formation of the skin layer 28 results in the product 30 being liquid impermeable. That is the product has a hydrohead of at least 50 centimeters of water when measured in accordance with Federal Test Method No. 5514, standard no. 191A.

In some embodiments, where it is desirable for the material to retain its liquid impermeability while still having the ability to "breathe", that is, pass water vapor, the liquid impermeable skin layer 26 may be provided with apertures of a size large enough to allow the passage of vapor, for example water vapor, but small enough to prohibit the passage of a liquid such as, for example, water. Apertures of this sort can be provided in accordance with the teachings of U.S. patent application Ser. No. 07/769,045 filed on Sep. 30, 1991 now U.S. Pat. No. 5,269,981 and entitled "Process for Microaperaturing Thin Sheet Materials". This application is hereby incorporated by reference in its entirety.

In those embodiments where the additional feature of "breathability" (water vapor transmission) is desired and the skin layer 28 is apertured, the product should have a water vapor transmission rate (measured in accordance with) of at least about 500 grams per square meter per day when measured in accordance with ASTM 96-80 while still remaining liquid impermeable. For example, the products may have a water vapor transmission rate of at least about 750 grams per square meter per day while still remaining liquid impermeable. More particularly, the products may have a water vapor transmission rate of at least about 1,000 grams per square meter per day while still remaining liquid impermeable.

Figure 4:
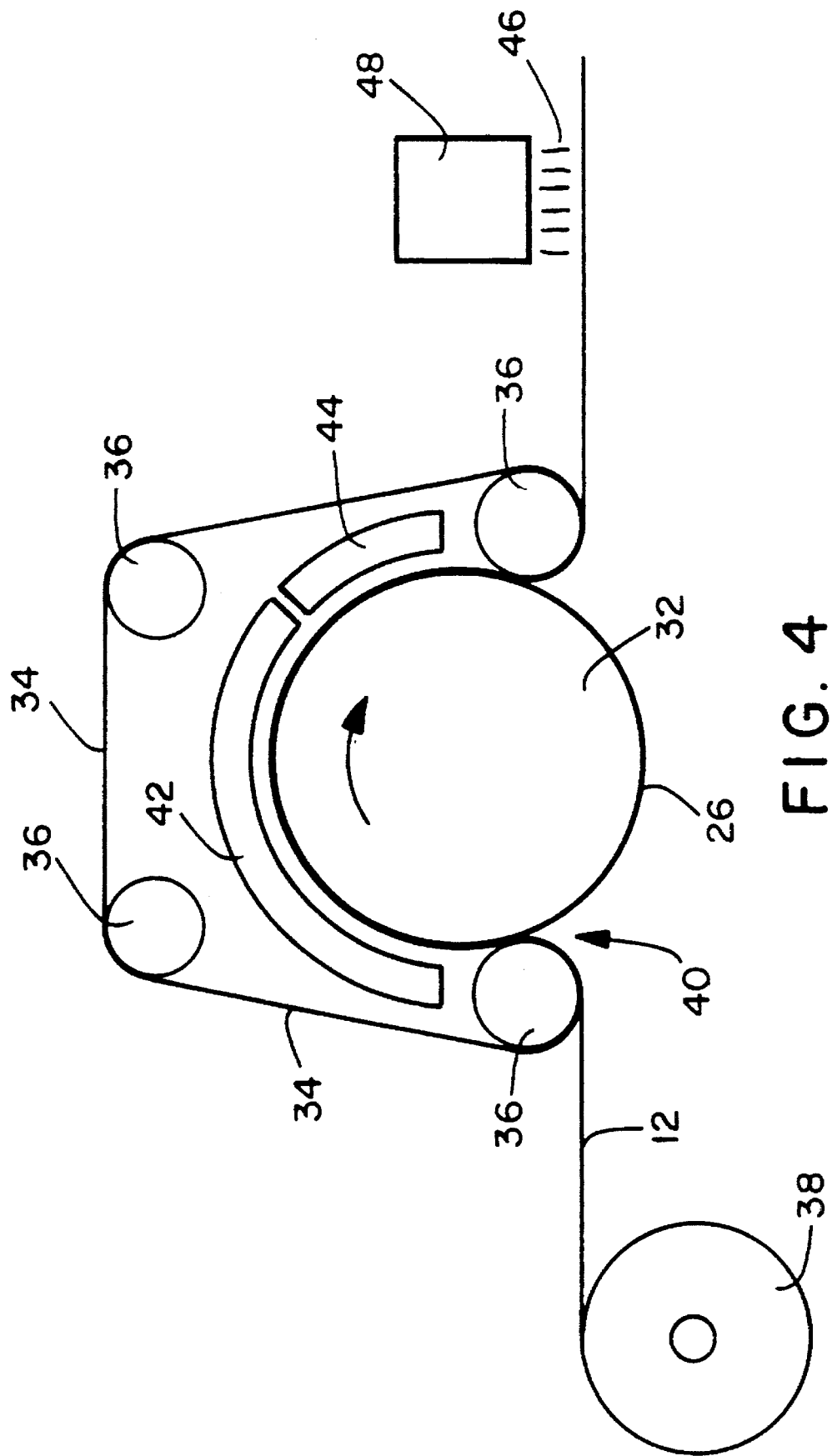
FIG. 4 is a schematic representation of another apparatus for performing present invention.

FIG. 4 illustrates a more automated and thus, possibly, more cost effective apparatus for forming the product 30 of the present invention. FIG. 4 illustrates a chill roll 32 which is provided with a resilient surface coating 26. A heat transfer band 34 is arranged around guide rollers 36 so that the band 34 is urged into a semi-circumferential engagement with the chill roll 32. A supply roll 38 of a fibrous web material 12 provides the web 12 to the nip 40 formed by the chill roll 32 and the band 34. An arched heating element 42 is located within the path of the band 34 downstream of the nip 40 for a first portion of the circumference of the chill roll 32. Downstream of the heating element 42, an arched cooling element 44 is located within the path of the band 34 for a second portion of the circumference of the chill roll 34. The arched heating element 42 and the arched cooling element are located in generally parallel arrangement to the surface of the chill roll 34 to, in the case of the heating element 42, provide a generally uniform application of thermal energy to the web 12 and, in the case of the cooling element 44, a generally uniform cooling effect.

Two of the functions that the heat transfer band 34 performs are (1) to transfer heat and cooling respectively from the heating element 42 and the cooling element 44 to the web 12 and (2) to apply the pressure required to form the melted fibers of the surface facing the heating element 42 into a liquid impermeable skin layer 28. It is believed that the skin layer 28 formation may well be enhanced if the heat transfer band 34 is operated at a velocity slightly higher or lower than the velocity of the chill roll 32. The believed effect of this velocity differential would be to slightly smear the melted fibers of the surface facing the heating elements and more rapidly and uniformly spread them into a liquid impermeable skin 28.

In some embodiments, where a final material having two outer fibrous surfaces sandwiching a liquid impermeable layer is desired, the cooling element would not be utilized and a conventional fiber 46 dispensing arrangement 48 would be positioned at a point where the skin layer 28 was still hot and tacky. Fibers 46 deposited at this point in the process would adhere to the hot, tacky skin layer 28 and yield a fibrous/skin/fibrous composite structure. Exemplary fibers that could be deposited at this point include staple fibers, meltblown fibers, spunbonded fibers and natural fibers such as, for example, cotton, wool and wood pulp fibers and fluff. Alternatively, particulates could be deposited upon the skin layer 28. Exemplary particulates include, without limitation, (1) odor absorbing particulates such as activated charcoal, zeolites and chitin; (2) superabsorbent particulates which have the ability to absorb at least ten (10) times their weight in water; and (3) electrically conductive particulates. Those of skill in the art will recognize that lamination of a self-supporting web or film to the tacky surface of the skin layer 28 could occur at this point also. However, the additional cost of a full-fledged lamination step would be incurred.

Further clarification of the present invention is afforded by reference to the following examples.

EXAMPLE I

The fibrous web selected for this example was a fine fiber meltblown polyethylene web. The web had a strong forming wire pattern on one side thereof as a result of its formation. The web was placed, forming wire pattern down, on a ⅛th inch thick steel plate which performed the function of a heat sink. A piece of Teflon® coated aluminum foil was placed over the; polyethylene web with the Teflon® side to the web. A commercial pressing iron was heated to its highest setting of about 204.4 degrees C. (about 400 degrees F.) and the soleplate of the iron was briefly pressed down of the foil surface. The foil was then lifted from the heat sink and the web removed. Most of the web was entirely filmed, but some of the area was filmed on one side with the fibers intact on the heat sink side.

EXAMPLE II

In order to generally duplicate the results of Example I with more control and reproducability, a different apparatus was assembled. First, a stirring hot plate with a 12 inch by 12 inch platen was cannibalized to make an inverted hot platen. The platen was provided with wooden handles and a ¼th inch thick stainless steel plate was attached to the bottom of the hot plate to act as the soleplate of the "iron". Power to the heat element was regulated by a variable autotransformer and the temperature of the soleplate was read by a contact thermocouple inserted through the well area of the stirring platen.

The heat sink and working surface was an aluminum plate approximately 20 inches by 15 inches by 5/8th inch in dimension. A sheet of silicon rubber about 1/32nd inch thick, 50 Shore A durometer, was placed over the aluminum plate. The sample to be treated was placed on the silicone sheet with the side intended to remain fibrous against the silicone sheet. A sheet of 0.003 inch thick Teflon® impregnated fiberglass woven cloth was used as a heat transfer/release interface. The Teflon® impregnated fiberglass woven cloth was placed over the sample to be "skinned" and the heating element was then passed over the cloth with an "ironing" motion to effect skin layer formation. As a result of the heating operation the 12 inch by 12 inch platen bowed So that the effective ironing surface was about 12 inches by 4 inches.

Several trials were conducted utilizing this method to determine appropriate operating variables which would effect skin layer formation. The fibrous web materials used in these trials were various basis weights of two different polypropylenes. The two polypropylene resins used were: (1) Himont PF 015 (obtained from Himont Corporation, Wilmington, Del.) which formed a web of fine soft fibers; and (2) Valtec HH441 which may be obtained from Himont Corporation, Wilmington, Del. The Valtec HH441 formed a web of large, coarse fibers. The melt flow of the Valtec HH441 is about 400 grams per ten minutes and the melt flow of the Himont PF015 is about 800 grams per ten minutes before the initial processing to form the initial fibers. The melt flow after initial formation is then about 600 grams per ten minutes for the Valtec HH441 and about 1200 grams per ten minutes for the Himont PF 015.

The diameter of the Himont PF 015 fibers ranged from about 5.5 microns to 7.5 microns. The diameter of the Valtec HH441 fibers ranged from about 14 microns to 16 microns.

A layer of fibrous web material made from Valtec HH441 with a basis weight of 0.3 ounces per square yard (osy) (7.11 grams per square meter) and measuring about 15 inches (38 centimeters) wide by 20 inches (50.8 centimeters) long was placed directly on the silicon rubber sheet. Two layers of a fibrous web made from Himont PF 015 with a basis weight of 0.7 osy (16.6 grams per square meter) and 0.5 osy (11.9 grams per square meter) were placed over the first layer. The layer of Valtec HH441 had a thickness of 2.8 mils (average of eight measurements on a TMI thickness measurement instrument Model 49-70, TMI Corporation, Amityville, L. I., N.Y.). The layer of 0.7 osy Himont PF 015 had a thickness of 5.0 mils and the layer of 0.5 osy Himont PF 015 had a thickness of 4.0 mils (measurement as for Valtec HH441). The final composite consisted of 0.3 osy Valtec HH441 as a first side and 1.2 osy Himont PF 015 as a second side. A Teflon® impregnated fiberglass cloth was placed over the composite. The platen was heated to 176.6 degrees C. (350 degrees F.) The platen was placed on the fiberglass cloth and a single "ironing" pass was made down the center of the length of the sample. The fiberglass cloth removed leaving a filmed strip about 4 inches wide down the center of the Himont PF 015 polymer surface. The Valtec HH441 polymer surface retained its fibrous quality.

EXAMPLE III

This sample consisted of a layer of 0.5 osy Valtec 441 web and a layer of 0.5 osy Himont PF 015 web. Fiber diameter of the Valtec HH441 ranged from 14 to 16 microns. Fiber diameter of the Himont PF 015 ranged from 5.5 microns to 7.5 microns. The total web thickness was 7.6 mils with the Valtec HH441 being 3.6 mils and the Himont PF 015 being 4.0 mils. The sample was treated as described in Example II. The sample after treatment was found to be partially filmed in the center strip.

EXAMPLE IV

This sample consisted of 0.5 osy Valtec HH441, 0.3 osy Valtec HH441 and 0.7 osy Himont PF 015. Both Valtec HH441 webs were placed on the Himont PF 015 web. The fiber diameters were as described in Example II. The web thickness are noted in Examples II and III. The treatment was the same as Example II except the platen was heated to 182.2 degrees C,. (360 degrees F.) The results were the same as obtained in Example III.

EXAMPLE V

This sample consisted of two 0.5 osy layers of Valtec HH441 web on one layer of 0.3 osy Himont PF 015 web. Fiber diameter and web thickness are as previously described. The 0.3 osy Himont PF 015 not previously described had a fiber diameter of 5.5 microns to 7.5 microns with a web thickness of 2.0 mils. The treatment was the same as in Example II except the platen was heated to 182.2 degrees C. (360 degrees F.) The sample after treatment showed complete filming of the Himont PF 015 web with the Valtec HH441 web retaining its fibrous character.

EXAMPLE VI

Example V was repeated. In this case three "ironing" passes were made down the length of the sample, one at the top, one in the center and one at the bottom. The filming was complete and covered the entire surface of the Himont PF 015. The Valtec HH441 web retained its fibrous character.

EXAMPLE VII

This sample and treatment was the same as Example VI except a downward force was applied to the heated platen and the platen moved faster across the sample. The results were the same as in Example VI.

EXAMPLE VIII

This sample and treatment was the same as Example VI except no downward force was applied and the platen was moved more slowly. The results were the same as in Example VI.

EXAMPLE IX

The sample and treatment was the same as in Example VI except in this case downward pressure was applied to the platen, the platen was moved more slowly and the temperature of the platen was about 173,8 degrees C. (345 degrees F.) The results were the same as in Example VI.

EXAMPLE X

Example IX was repeated with the platen at about 176.6 degrees C. (350 degrees F.) The results were the same as in Example IX.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and all equivalents thereto.

What is claimed is:

1. A process for forming a liquid-impermeable, breathable sheet having a fibrous surface, the process comprising the steps of:

forming a sheet having a first fibrous surface and a second fibrous surface;

subjecting the sheet to pressure and a z-gradient temperature differential sufficient to melt the fibers of the first surface and form the melt into a liquid impermeable, non-breathable skin without significantly altering the fibers of the second surface;

depositing fibers upon the skin while the skin is at least semi-molten to form a fibrous/skin/fibrous material; and aperturing the liquid impermeable, non-breathable skin to make it breathable, while the skin remains liquid-impermeable.

2. The process according to claim 1, wherein the z-gradient temperature differential is at least about 140 degrees C.

3. The process according to claim 1, wherein the z-gradient temperature differential is at least about 150 degrees C.

4. The process according to claim 1, wherein the z-gradient temperature differential is at least about 160 degrees C.

5. The process according to claim 1, wherein the apertures are microapertures.

6. A process for forming a liquid-impermeable, breathable sheet having a fibrous surface, the process comprising the steps of:

forming a sheet having a first fibrous surface and a second fibrous surface wherein, upon the sheet being subjected to a sufficient temperature, the fibers comprising the first fibrous surface are adapted to substantially completely melt prior to the fibers comprising the second fibrous surface significantly melting; and subjecting the sheet to a sufficient pressure and temperature to melt the fibers of the first surface and form the melt into a liquid impermeable, non-breathable skin without significantly altering the fibers of the second surface; and aperturing the liquid impermeable, non-breathable skin to make it breathable while the skin remains liquid-impermeable.

7. The process according to claim 6, wherein the fibers forming the first surface are formed from a material having a melt flow rate which is at least 25 percent greater than the melt flow rate of the material forming the fibers of the second surface.

8. The process according to claim 6, wherein the fibers forming the first surface are formed from a material having a melt flow rate which is at least 50 percent greater than the melt flow rate of the material forming the fibers of the second surface.

9. The process according to claim 6, wherein the fibers forming the first surface are formed from a material having a melt flow rate which is at least 100 percent greater than the melt flow rate of the material forming the fibers of the second surface.

10. The process according to claim 6, wherein the fibers forming the first and second surfaces are formed from one or more materials selected from the group consisting of polyolefins, polyesters, polyamides, polyurethanes and polyetheresters.

11. The process according to claim 6, wherein the fibers forming the first surface have an average diameter which is at least about 90 percent less than the average diameter of the fibers forming the second surface.

12. The process according to claim 6, wherein the fibers forming the first surface have an average diameter which is at least about 75 percent less than the average diameter of the fibers forming the second surface.

13. The process according to claim 6, wherein the fibers forming the first surface have an average diameter which is at least about 50 percent less than the average diameter of the fibers forming the second surface.

14. The process according to claim 6, wherein the apertures are microapertures.

15. The process according to claim 6, wherein the step of subjecting the sheet to pressure and temperature includes subjecting the sheet to a z-gradient temperature differential whereby the fibers comprising the first fibrous surface are subjected to a higher temperature than the fibers comprising the second fibrous surface.

16. A process for forming a liquid-impermeable, non-breathable sheet having a fibrous surface, the process comprising the steps of:

forming a sheet having a first fibrous surface and a second fibrous surface;

subjecting the sheet to pressure and a z-gradient temperature differential sufficient to melt the fibers of the first surface and form the melt into a liquid impermeable, non-breathable skin without significantly altering the fibers of the second surface; and depositing fibers upon the skin while the skin is at least semi-molten to form a fibrous/skin/fibrous material.

17. The process according to claim 16, wherein the z-gradient temperature differential is at least about 140 degrees C.

18. The process according to claim 16, wherein the z-gradient temperature differential is at least about 150 degrees C.

19. The process according to claim 16, wherein the z-gradient temperature differential is at least about 160 degrees C.

20. A process for forming a liquid-impermeable, non-breathable sheet having a fibrous surface, the process comprising the steps of:

forming a sheet having a first fibrous surface and a second fibrous surface wherein, upon the sheet being subjected to a sufficient temperature, the fibers comprising the first fibrous surface are adapted to substantially completely melt prior to the fibers comprising the second fibrous surface significantly melting; and subjecting the sheet to a sufficient pressure and temperature to melt the fibers of the first surface and form the melt into a liquid impermeable, non-breathable skin without significantly altering the fibers of the second surface.

21. A process for forming a liquid-impermeable, breathable sheet having a fibrous surface, the process comprising the steps of:

forming a sheet having a first fibrous surface and a second fibrous surface;

subjecting the sheet to pressure and a z-gradient temperature differential sufficient to melt the fibers of the first surface and form the melt into a liquid impermeable, non-breathable skin without significantly altering the fibers of the second surface;

depositing particulates upon the skin while the skin is at least semi-molten to form a fibrous/skin/particulate material; and aperturing the liquid impermeable, non-breathable skin to make it breathable, while the skin remains liquid-impermeable.

22. The process according to claim 21, wherein the z-gradient temperature differential is at least about 140 degrees C.

23. The process according to claim 21, wherein the z-gradient temperature differential is at least about 150 degrees C.

24. The process according to claim 21, wherein the z-gradient temperature differential is at least about 160 degrees C.

25. The process according to claim 21, wherein the apertures are microapertures.

26. A process for forming a liquid-impermeable, breathable sheet having a fibrous surface, the process comprising the steps of:

forming a sheet having a first fibrous surface and a second fibrous surface wherein, upon the sheet being subjected to a sufficient temperature, the fibers comprising the first fibrous surface are adapted to substantially completely melt prior to the fibers comprising the second fibrous surface significantly melting; and subjecting the sheet to a sufficient pressure and temperature to melt the fibers of the first surface and form the melt into a liquid impermeable, non-breathable skin without significantly altering the fibers of the second surface;

depositing fibers upon the skin while the skin is still at least semi-molten to form a fibrous/skin/fibrous material; and aperturing the liquid impermeable, non-breathable skin to make it breathable while the skin remains liquid-impermeable.

27. A process for forming a liquid-impermeable, breathable sheet having a fibrous surface, the process comprising the steps of:

forming a sheet having a first fibrous surface and a second fibrous surface wherein, upon the sheet being subjected to a sufficient temperature, the fibers comprising the first fibrous surface are adapted to substantially completely melt prior to the fibers comprising the second fibrous surface significantly melting;

subjecting the sheet to a sufficient pressure and temperature to melt the fibers of the first surface and form the melt into a liquid impermeable, non-breathable skin without significantly altering the fibers of the second surface;

depositing particulates upon the skin while the skin is still at least semi-molten to form a fibrous/skin/particulate material; and aperturing the liquid impermeable, non-breathable skin to make it breathable while the skin remains liquid-impermeable.

28. A process for forming a liquid-impermeable, non-breathable sheet having a fibrous surface, the process comprising the steps of:

forming a sheet having a first fibrous surface and a second fibrous surface;

subjecting the sheet to pressure and a z-gradient temperature differential sufficient to melt the fibers of the first surface and form the melt into a liquid impermeable, non-breathable skin without significantly altering the fibers of the second surface; and depositing particulates upon the skin while the skin is at least semi-molten to form a fibrous/skin/particulate material.

29. The process according to claim 28, wherein the z-gradient temperature differential is at least about 140 degrees C.

30. The process according to claim 28, wherein the z-gradient temperature differential is at least about 150 degrees C.

31. The process according to claim 28, wherein the z-gradient temperature differential is at least about 160 degrees C.

32. A process for forming a liquid-impermeable, non-breathable sheet having a fibrous surface, the process comprising the steps of:

forming a sheet having a first fibrous surface and a second fibrous surface wherein, upon the sheet being subjected to a sufficient temperature, the fibers comprising the first fibrous surface are adapted to substantially completely melt prior to the fibers comprising the second fibrous surface significantly melting;

subjecting the sheet to a sufficient pressure and temperature to melt the fibers of the first surface and form the melt into a liquid impermeable, non-breathable skin without significantly altering the fibers of the second surface; and depositing fibers upon the skin while the skin is still at least semi-molten to form a fibrous/skin/fibrous material.

33. A process for forming a liquid-impermeable, non-breathable sheet having a fibrous surface, the process comprising the steps of:

forming a sheet having a first fibrous surface and a second fibrous surface wherein, upon the sheet being subjected to a sufficient temperature, the fibers comprising the first fibrous surface are adapted to substantially completely melt prior to the fibers comprising the second fibrous surface significantly melting;

subjecting the sheet to a sufficient pressure and temperature to melt the fibers of the first surface and form the melt into a liquid impermeable, non-breathable skin without significantly altering the fibers of the second surface; and depositing particulates upon the skin while the skin is still at least semi-molten to form a fibrous/skin/particulate material.

\* \* \* \* \*